United States Patent
Halamek et al.

(10) Patent No.: US 8,600,485 B2
(45) Date of Patent: Dec. 3, 2013

(54) METHOD OF VENTRICULAR REPOLARIZATION ANALYSIS

(75) Inventors: Josef Halamek, Brno (CZ); Pavel Jurak, Brno (CZ)

(73) Assignee: Institute of Scientific Instruments of the ASCR, V.V.I., Brno (CS)

( * ) Notice: Subject to any disclaimer, the term of this patent is extended or adjusted under 35 U.S.C. 154(b) by 1011 days.

(21) Appl. No.: 12/601,550

(22) PCT Filed: Jun. 2, 2008

(86) PCT No.: PCT/IB2008/002198
§ 371 (c)(1),
(2), (4) Date: Dec. 9, 2009

(87) PCT Pub. No.: WO2008/146168
PCT Pub. Date: Dec. 4, 2008

(65) Prior Publication Data
US 2010/0174203 A1 Jul. 8, 2010

(30) Foreign Application Priority Data

May 30, 2007 (CZ) .................................. 2007-376

(51) Int. Cl.
*A61B 5/0452* (2006.01)
(52) U.S. Cl.
USPC ........... 600/509; 600/508; 600/512; 600/513; 600/514; 600/515; 600/516; 600/517; 600/518; 600/519; 600/521
(58) Field of Classification Search
USPC .......................... 600/508–509, 512–519, 521
See application file for complete search history.

*Primary Examiner* — Deborah Malamud
(74) *Attorney, Agent, or Firm* — Notaro, Michalos & Zaccaria P.C.

(57) ABSTRACT

While analyzing ventricular repolarization in accordance with the invention, ECG measurement with excitation of heart rate is evaluated and the coupling of an internal parameter, for example QT to heartbeat interval, for example RR, is modeled by a transfer function with three parameters. The values of the resulting five parameters describing the static and dynamic characteristics of ventricular repolarization are obtained by means of transfer function parameters and the measured values of heart rate and the internal parameter. The effect of medication is evaluated from the difference of the values of these parameters determined before and after administrating the medication.

7 Claims, 2 Drawing Sheets

METHOD OF VENTRICULAR REPOLARIZATION ANALYSIS

TECHNICAL FIELD

The invention concerns ventricular repolarization analysis based on electrocardiogram.

BACKGROUND ART

Ventricular depolarization and repolarization of the heart muscle, represented by QT intervals detected by an electrocardiogram (ECG), is an important variable for the prediction of sudden cardiac death or ventricular arrhythmia, known as Torsade de Pointes (TdP), and is used for the classification of patients with long and short QT intervals. All medication must be tested in order to find out whether or not it has an effect on QT intervals. There is a relation between QT intervals and heart rate, defined by RR intervals. Analysis of the QT/RR coupling is one of the primary problems in the evaluation of QT interval abnormalities and the effect of medication on QT intervals. In spite of the fact that a lot of research units are investigating this issue, there is no model or comprehensive list of parameters describing the static and dynamic characteristics of the QT/RR coupling.

QTc is the basic parameter in use. It is a recalculated QT interval for the RR interval, which equals 1 second. The QTc parameter is calculated by means of a non-linear static correction considering the dependence only on the previous RR interval. Many corrections based on various types of non-linear static function have been proposed. Bazett's correction, derived as far back as 1920, is still the most commonly used, but also the most criticized. It has been shown that QTc is not an adequate parameter for characterization of ventricular depolarization and repolarization: it is merely a static parameter. The dynamic characteristics of the connection are not considered in QTc calculation, although it is known that TdP is induced by a sudden change in RR intervals caused, for example, by stress or physical strain. A large number of published corrections also raise doubts about the correct calculation of the QTc value by means of non-linear, static dependence.

Other parameters used to characterize QT/RR coupling are the delay with which QT attains a steady state, QT "dynamics", QT/RR variability, and graphic analysis. Porta and Almeida used a higher order transfer function, with eight or more parameters, to characterize QT/RR coupling during individual measurements, with the selected function order being optimized for a given measurement. The number and type of parameters applied were different for individual measurements. However, they analyzed only short measurements at rest. They were not able to define a general model and characteristics of QT/RR coupling. There is no comprehensive set of parameters that would enable an objective assessment of ventricular repolarization of a particular subject or an objective evaluation of the effect of medication.

Ventricular repolarization is sometimes analyzed from other intervals detected from ECG, such as RT, RTmax and QTmax intervals. The problems facing evaluation are the same as those for the QT interval.

The aim of this invention is to provide a method that would enable an integrated set of parameters describing the static and dynamic characteristics of repolarization to be obtained. This set of parameters would be used for evaluation of the effect of medication on patients' health.

DISCLOSURE OF THE INVENTION

The aim given above is achieved by means of ventricular repolarization analysis based on electrocardiogram designed in accordance with this invention. The principle is to measure a continuous ECG with a distinct, prolonged change in heart rate, for example at rest, during increased heart rate, and then at rest again. A continuous sequence of CD pulse intervals and AB internal intervals is detected from the measured ECG signal. From the acquired AB and CD values it is then possible to determine instrumental variables CDx=CD−mean(CD) and ABx=AB−mean(AB). Subsequently, by means of minimization of the mean quadratic deviation over the whole course of measurement between the measured values of internal ABx intervals and model ABmx values, given by the formula $$abmx(i) = b_{k+1} cdx(i-k) + b_{k+2} cdx(i-k-1) - a_1 abmx(i-1),$$

where $cdx(i)$ and $abmx(i)$ are i-th values of variables CDx and ABmx and k is the primary delay between the variables, the values of parameters $a_1$, $b_{k+1}$, $b_{k+2}$ of the transfer function $$H_{ABx/CDx}(z) = \frac{b_{k+1} z^{-k} + b_{k+2} z^{-(k+1)}}{1 + a_1 z^{-1}}$$

are determined.

Subsequently, the frequency and step response of the AB/CD coupling is determined by means of this transfer function. The response defines three parameters of physiological relevance—a transfer gain ($Gain_S$) between AB variability and CD variability for slow changes in heartbeat intervals CD, given by the amplitude of steady change AB with a unit-step function of heartbeat intervals CD, a transfer gain ($Gain_F$) for rapid changes in heartbeat intervals CD, given by the amplitude of the immediate change in AB interval with a unit-step function of heartbeat intervals CD, and the number of heart-beats (T), when the value of the AB interval reaches a certain percentage of the steady state after a step change of heartbeat intervals CD. Then, on the basis of the transfer gain value between the AB variability and CD variability for slow changes acquired this way, the corrected value ABc for the excitation used during measurement is determined by means of the equation $$ABc = ABst + (1 - CDst) \cdot Gain_S,$$

where ABst and CDst are the mean values of the steady state of the AB and CD intervals. On the basis of ABmx, it is then possible to calculate the model value $$Abm = ABmx + \text{mean}(AB),$$

which is used for the calculation of AB variability independent of CD intervals. The value given as ABvar is the variability of the difference AB−ABm. The acquired values of the transfer gain between the AB variability and CD variability for slow changes in heartbeat intervals CD, the transfer gain between the AB variability and CD variability for rapid changes of heartbeat intervals CD, the number of heart beats, when the value of the AB interval reaches a certain percentage of the steady state after a step change of heartbeat intervals CD, the variability of the AB interval independent of CD and corrected value ABc, are subsequently used as the characteristic values for the evaluation of ventricular repolarization. This invention then uses the RR interval as the heartbeat interval and the QT interval or one of the RT, Qtmax or Rtmax intervals as the internal AB interval. In all these cases, the baseline delay between the variables is 1 heart beat, that is k=1, so the transfer function is:

$$H_{QTx/RRx}(z) = \frac{b_2 z^{-1} + b_3 z^{-2}}{1 + a_1 z^{-1}}.$$

For the definition of heartbeat intervals CD it is, instead of the RR interval, also possible to use the TT or TQ intervals, where the coupling between fill and blood expulsion intervals in the same heart beat is evaluated, for which reason there is no baseline delay of 1 heart beat, k=0. Then the transfer function is:

$$H_{QTx/TTx}(z) = \frac{b_1 + b_2 z^{-1}}{1 + a_1 z^{-1}}.$$

Likewise, according to this invention, the entire procedure is performed at least once before administrating the tested medication and at least once after administrating the tested medication, at the time of the expected effect of the medication, and the effect of the medication is determined on the basis of the difference of the values of the parameters describing ventricular repolarization recorded before and after administrating the medication.

When ventricular repolarization is analyzed with this invention, ECG measurement is evaluated with the excitation of heart rate, and the coupling of the internal AB parameter with the heart rate is modeled by a transfer function with three parameters. By means of the transfer function parameters and the measured values of heart rate and the internal AB parameter, it is possible to obtain the values of the resulting five parameters—$Gain_S$, $Gain_F$, T, ABc and ABvar, characterizing ventricular repolarization. The advantage of this invention is that the acquired values reflect not only the static, but also the dynamic characteristics of ventricular repolarization of the heart muscle and therefore become objective indicators providing a comprehensive characterization of all changes in ventricular repolarization arising as a result of medication.

DESCRIPTION OF FIGURES

The invention is further explained in more details against examples of its performance, and by means of pictures given in the enclosed drawings.

EXAMPLES OF PERFORMANCE

Figure 1:
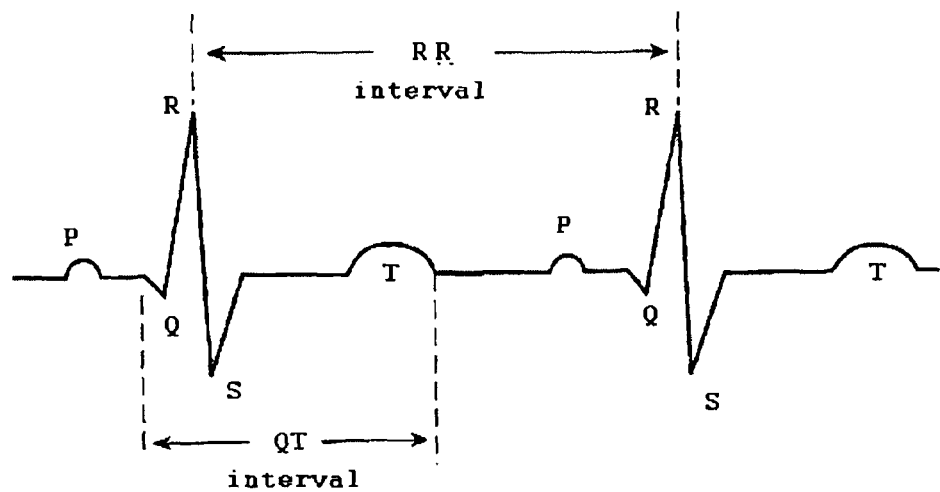
FIG. 1 shows a model ECG signal with important waves and individual intervals marked.

Continuous ECG at rest, at increased heart beat and then again at rest is first measured using the given invention. An example of one model ECG heart beat with characteristic points marked is shown in FIG. 1. CD heartbeat intervals and internal AB intervals are detected from the observed ECG recording. QT intervals, RT intervals and Qtmax or Rtmax intervals are examples of internal AB intervals. CD heartbeat intervals are, for example, the RR interval, TT interval or TQ interval.

The detected intervals must represent a uninterrupted sequence, without any intervals left out, in order to be able to analyze the dynamic processes. The auxiliary variables are determined from the acquired values of internal intervals and heartbeat intervals $$CDx = CD - \text{mean}(CD),$$

$$ABx = AB - \text{mean}(AB).$$

Subsequently, by minimizing the mean quadratic (R.M.S.) deviation over the whole course of measurement between the measured ABx and model ABmx given by the following formula $$abmx(i) = b_{k+1} cdx(i-k) + b_{k+2} cdx(i-k-1) - a_1 abmx(i-1),$$

where cdx(i) and abmx(i) are i-th values of variables CDx and ABmx and k is the baseline delay between the variables and is equal to 1 for all internal intervals and heartbeat intervals RR or equal to 0 for heartbeat intervals TT or TQ, the values of parameters $a_1$, $b_{k+1}$ and $b_{k+2}$ of the transfer function are acquired $$H_{ABx/CDx}(z) = \frac{b_{k+1} z^{-k} + b_{k+2} z^{-(k+1)}}{1 + a_1 z^{-1}},$$

and then the frequency and step response of AB/CD coupling are determined by means of this transfer function, thereby defining three parameters of physiological relevance, namely Transfer gain ($Gain_S$) between AB variability and CD variability for slow changes in heart rate, given by the extent of steady change of AB interval during a unit step of heartbeat intervals CD.

Transfer gain ($Gain_F$) between AB variability and CD variability for rapid changes in heart rate, given by the amplitude of an instantaneous change of AB internal during a unit step of heartbeat intervals CD, Number of T heartbeats, when the value of interval AB reaches a certain percentage of the steady state after a step change of heartbeat intervals CD.

On the basis of the value acquired in this way for module $Gain_S$ for slow changes in heart rate, a corrected value ABc for the excitation used during measurement is determined by means of this formula:

$$ABc = ABst + (1 - CDst) \cdot Gain_S,$$

where ABst and CDst are mean values of a steady state of internal intervals AB and heartbeat intervals CD and, on the basis of ABmx, the model value $$Abm = ABmx + \text{mean}(AB),$$

is determined, which is used to calculate the AB interval variability independent of the CD interval. The value of ABvar variability is the variability of the AB–ABm difference. Subsequently, the acquired value of the $Gain_S$ module of transmission for slow changes of heartbeat interval, the value of the $Gain_F$ module of transmission for rapid changes of heartbeat interval, the number of T heart-beats, when the value of the AB interval reaches a certain percentage of the steady state after a step change of heartbeat intervals, ABvar, variability of the AB interval independent of heart rate and corrected value of ABc, as the characteristic value, are used for the evaluation of ventricular repolarization.

In order to assess the effect of medication on ventricular depolarization of the heart muscle, it is necessary to carry out the entire procedure given above at least once before administrating the tested medication and at least once after administrating the tested medication, and the effect of the medication is determined on the basis of the difference in values measured before and after administrating the medication.

Example 1

Figure 2:
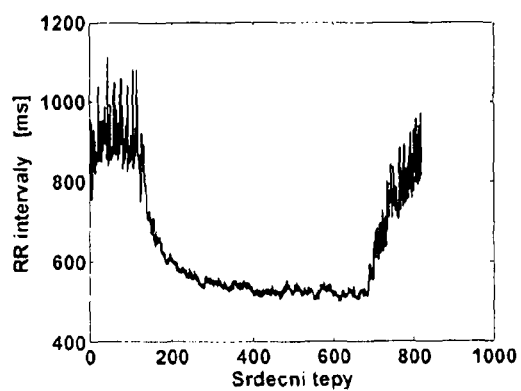
FIG. 2 shows the detected RR intervals.
Figure 3:
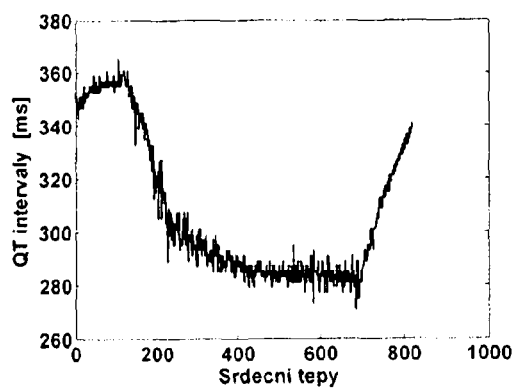
FIG. 3 illustrates the detected QT intervals.

The measurement is represented by a continuous ECG recording over the course of 3 minutes at rest, 5 minutes during physical strain, and then 2 minutes at rest again. The detected RR intervals are given in FIG. 2, the detected QT intervals are in FIG. 3.

Optimized invariables $a_1=-0.9775$, $b_2=0.0127$ and $b_3=-0.0084$ were determined from the measured values of the RR intervals and QT intervals by means of the transfer function in the following formula $$H_{QTx/RRx}(z) = \frac{b_2 z^{-1} + b_3 z^{-2}}{1 + a_1 z^{-1}}.$$

Figure 4:
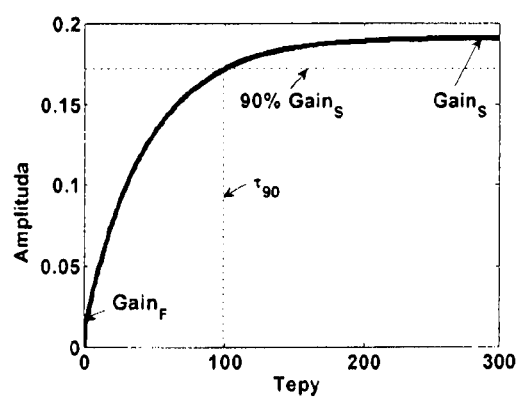
FIG. 4 represents the calculated step response.
Figure 5:
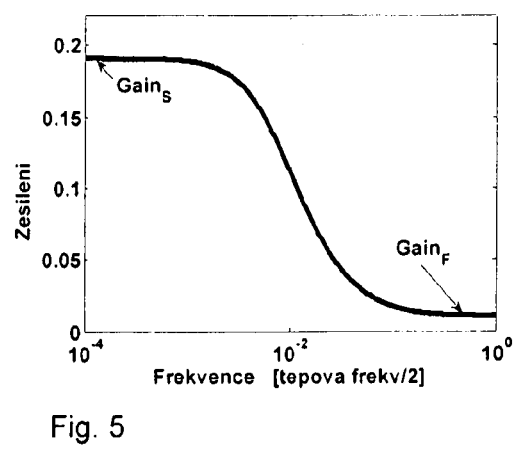
FIG. 5 shows the frequency characteristic.

The calculated step response is given in FIG. 4, the frequency characteristic is in FIG. 5.

From here, values $Gain_S=0.191$, $Gain_F=0.011$ and $T=99$., value $QTvar=3.83$ ms and value $QTc=373$ ms were determined.

Deviations of the detected QT from the model are shown in FIG. 6.

All processing can proceed automatically. An check is appropriate merely for QT interval detection.

Example 2

When analyzing ventricular repolarization by the given method, it is possible to proceed in a similar way as in Example 1, though using other internal AB intervals detected from ECG recording, for example RT intervals or QTmax intervals or RTmax intervals, instead of the QT interval, and their relation to heartbeat intervals RR is considered. Delay k=1, so the formula of the transfer function is $$H_{ABx/RRx}(z) = \frac{b_2 z^{-1} + b_3 z^{-2}}{1 + a_1 z^{-1}}.$$

Example 3

It is also possible to evaluate the relation between blood fill and expulsion intervals in the same heartbeat, with other CD intervals, i.e. TT or TQ intervals, used instead of the RR interval. In this case the baseline delay of 1 beat between the variables is not considered, as in the transmission formula given in Examples 1 and 2, though the formula for the transfer function is $$H_{ABx/CDx}(z) = \frac{b_1 + b_2 z^{-1}}{1 + a_1 z^{-1}}.$$

Similarly as in Example 1 it is possible to use parameters $b_1$, $b_2$ and $a_1$ of the transfer function to determine the value of the $Gain_S$ module of transmission for slow changes of heart rate, the value of the $Gain_F$ module of transmission for rapid changes of heart rate, number of T heart-beats, when the value of the AB interval reaches a certain percentage of the steady state after a step change of heartbeat intervals and, subsequently, the ABvar value, variabilities of the AB interval independent of heart rate and the corrected ABc value. These characteristic values again serve for the evaluation of ventricular repolarization, as described above.

INDUSTRIAL APPLICABILITY

The given method is suitable for the pharmaceutical industry, for the evaluation of medication from the viewpoint of its effect on ventricular repolarization of the heart muscle.

The invention claimed is:
1. A method of ventricular repolarization analysis using an electrocardiogram, the method comprising the steps of:
providing an ECG machine and coupling the ECG machine to a patient,
using the ECG machine to measure a continuous course of ECG of the patient at rest, then at increased heart rate, and then at rest again,
determining a continuous succession of heartbeat intervals CD and internal intervals AB within the measured ECG signal and instrumental variables using the measurements made using ECG,
determining

$CDx=CD-\text{mean}(CD)$, and $ABx=AB-\text{mean}(AB)$ from the detected AB and CD values, then,
determining parameters $a_1$, $b_{k+1}$, and $b_{k+2}$ by means of minimization of the mean quadratic deviation in the whole course of measurement between the measured ABx intervals and model ABmx values, which determination is made using the formula $ABmx(i)=b_{k+1}CDx(i-k)+b_{k+2}CDx(i-k-1)-a_1ABmx(i-1)$, where CDx(i) and ABmx(i) are the i-th values of the CDx and ABmx variables and wherein k is delay between variables,
determining frequency and step response of AB/CD couplings using a transfer function $$H_{ABx/CDx}(z) = \frac{b_{k+1} z^{-k} + b_{k+2} z^{-(k+1)}}{1 + a_1 z^{-1}}$$

determining the following three parameters of physiological relevance by means of said transfer function:
transfer gain ($Gain_S$) between AB variability (ABvar) and CD variability for slow changes in heart rate given by the extent of steady change AB at a unit step CD,
transfer gain ($Gain_F$) for rapid changes in heart rate, given by the amplitude of an instantaneous change of AB interval at unit step CD, and
number of T heartbeats, when the value of the AB interval reaches a certain percentage of the steady state after a step change of CD intervals;
determining a corrected value ABc for the excitation used during measurement by means of the formula:

$ABc=ABst+(1-CDst)\cdot Gain_S$, where ABst and CDst are mean values of the steady state of intervals AB and CD,
determining a model value ABm using the formula:

$ABm=ABmx+\text{mean}(AB)$, and using the model value ABm to calculate the AB variability (ABvar) independent of the CD interval, wherein ABvar is the variability of the difference AB−ABm, and evaluating ventricular polarization using at least one of said determined parameters $Gain_S$, $Gain_F$, T heartbeats, ABc, and ABvar.

2. The method of ventricular repolarization analysis in accordance with claim 1 further characterized by using one of QT, RT, QTmax or RTmax intervals as the internal AB interval, and using an RR interval as heartbeat interval CD, where the formula of the transfer function is $$H_{ABx/RRx}(z) = \frac{b_2 z^{-1} + b_3 z^{-2}}{1 + a_1 z^{-1}}.$$

3. The method of ventricular repolarization analysis in accordance with claim 2 characterized by measuring of the continuous ECG using the ECG machine across a time span including a prolonged change in heart rate in the patient.

4. The method of ventricular repolarization analysis in accordance with claim 2, further characterized by:

performing the entire procedure of claim 2 at least once before administrating a medicine to be tested to the patient, and repeating the procedure at least once after administrating the tested medicine, and determining the effect of the medicine by comparing the values of parameters based on measurements taken by the ECG machine before and after administrating the medicine.

5. The method of ventricular repolarization analysis in accordance with claim 1 further characterized by using one of QT, RT, QTmax or RTmax intervals as the AB interval, and one of TT or TQ intervals as heartbeat interval CD, where the formula of the transfer function is $$H_{ABx/CDx}(z) = \frac{b_1 + b_2 z^{-1}}{1 + a_1 z^{-1}}.$$

6. The method of ventricular repolarization analysis in accordance with claim 1 characterized by measuring of the continuous ECG using the ECG machine across a time span including a prolonged change in heart rate in the patient.

7. The method of ventricular repolarization analysis in accordance with claim 1, further characterized by:

performing the entire procedure in claim 1 at least once before administrating a medicine to be tested, and repeating the procedure at least once after administrating the tested medicine to the patient, and determining the effect of the medicine on the patient by comparing the values of parameters based on measurements taken by the ECG machine before and after administrating the medicine.

\* \* \* \* \*